US00PP12255P2

(12) United States Plant Patent
Drewlow

(10) Patent No.: US PP12,255 P2
(45) Date of Patent: Dec. 4, 2001

(54) NEW GUINEA IMPATIENS PLANT NAMED 'OVATION BLUSH PINK'

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/556,284

(22) Filed: Apr. 24, 2000

(51) Int. Cl.[7] ..... A01H 5/00

(52) U.S. Cl. ..... Plt./318
(58) Field of Search ..... Plt./318

*Primary Examiner*—Bruce R. Campell
*Assistant Examiner*—Anne Marie Grünberg
(74) *Attorney, Agent, or Firm*—Webb Ziesenheim Logsdon Orkin & Hanson, P.C.

(57) ABSTRACT

A distinct cultivar of Impatiens plant named Ovation Blush Pink, characterized by its blush pink flower color, large flower diameter, solid dark green leaves, early flowering, long-lasting flowering, and highly self-branching and vigorous habit.

1 Drawing Sheet

The present invention relates to a new and distinctive cultivar of Impatiens plant, botanically known as *Impatiens hawkeri*, commercially known as New Guinea Impatiens, and known by the cultivar name 'Ovation Blush Pink'. Ovation Blush Pink was developed in a controlled breeding program by crossing Samoa (U.S. Plant Pat. No. 8,422) (seed parent) with Mikkelsen Seedling No. 95-397-1 (pollen parent). The pollen parent is a proprietary breeding line which has not been sold or made publicly available in this country.

Asexual reproduction carried out by the inventor in Lompoc, Calif. by terminal or stem cuttings has shown that the unique features of this new Impatiens are stabilized and are reproduced true to type in successive propagations.

The following combination of characteristics distinguish the new Impatiens from both its parent varieties and other cultivated Impatiens of this type known and used in the floriculture industry:

1. Ovation Blush Pink is intermediate in color between Improved Samoa (U.S. Plant Pat. No. 9,138) having less pink blushing and Celebration Blush Pink (patent pending) which has more blushing.

2. Ovation Blush Pink has a larger flower (7.0 to 7.5 cm) than Improved Samoa and Celebration Blush Pink which both have 6.0 to 6.5 cm flowers.

3. Ovation Blush Pink has dark green foliage with Celebration Blush Pink having bright green foliage and Improved Samoa intermediate green foliage.

4. Ovation Blush Pink has shorter broader leaves than either Improved Samoa and Celebration Blush Pink which both have longer narrower leaves.

5. Ovation Blush Pink has a mounded growth habit with Celebration Blush Pink being more upright with Improved Samoa having an intermediate habit.

6. The leaves of Ovation Blush Pink do not show curling under high light condition as do the leaves of Improved Samoa and Celebration Blush Pink.

7. Ovation Blush Pink has a deep red cast to its branches with Celebration Blush Pink having a lesser red cast and Improved Samoa intermediate.

8. Ovation Blush Pink is superior to both Improved Samoa and Celebration Blush Pink in continuing to bloom under high temperature outside summer conditions.

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. The plants were grown at 16° C. night temperatures, under 3000 to 4000 foot candles of light and 200 ppm nitrogen, 75 ppm potassium, and 200 ppm phosphorous with nutritional trace elements added. Habit of growth, foliage coloration, leaf variegation, size of leaves and flower size will be greatly influenced by nutritional and environmental conditions.

Color references are made to The Royal Horticultural Society Colour Chart except where general terms of ordinary dictionary significance are used.

Parentage: A controlled cross between female plant Samoa (U.S. Plant Pat. No. 8,422) and male parent Mikkelsen Seedling No. 95-397-1.

Propagation:

(*A*) *Type cutting.*—Stem tip 15 mm long will develop to 4 to 5 cm long in 18 to 21 days.

(*B*) *Time to root.*—8–10 days at 23° C. summer; 10–12 days at 20° C. winter.

(*C*) *Rooting habit.*—Heavy, fiborous.

Plant description:

(*A*) *Form and habit of gowth.*—Mounded, self-branched, intermediate in height, flowers open over the top of leaf canopy; continuous flowering; vigorous growing flowering herb. Average height is 18 to 22 cm and average width is 40 to 45 cm. Internode length is 6 to 7 cm but is highly variable. Pedicel is Greyed-Purple Group 184C, stem is Greyed-Purple Group 185A, and internode is Greyed-Purple Group 185A. Pedicel length is 4.5 cm.

(*B*) *Foliage description.*—Dark green with brownish red cast, especially on underside of leaves; red-purple midrib and no leaf variegation. (1) Size: 7 to 8 cm long and 3.0 to 3.5 cm wide on average mature leaf. (2) Shape: Lanceolate with acuminate apex and acute base. (3) Texture: Both upper and lower surfaces are glabrous. (4) Margin: Entire, with fine cilia.

(5) Color: Young foliage, top side is Yellow-Green Group 147A, underside is Greyed-Purple Group 183C. Mature foliage, top side is Yellow-Green Group 147A, underside is Greyed-Purple Group 183C. (6) Venation: Pinnate, upper side is Yellow-Green Group 148B and lower side is Greyed-Purple Group 184B. (7) Young midrib is Greyed-Purple Group 185B and mature midrib is Greyed-Purple Group 184C.

(*C*) *Branching.*—The branching is naturally occurring and has a Greyed-Purple Group 185A cast. Lateral branching at base: 5 or more lateral branches. Lateral branch length is 12 to 15 cm but is highly variable.

Flowering description:

(*A*) *Flowering habits.*—Flowers continously from leaf whorl in a progressively orderly manner with one flower per leaf axil. When the last flower in a whorl opens the first flower in the leaf whorl above starts to open. It takes 5 to 7 days for a mature bud to fully open and the flower may last two weeks or longer depending on the environment. The time to first flower is aproximately 8 weeks from root cuttings. The flowers are self-cleaning.

(*B*) *Natural flowering season.*—Indeterminant and continuous; quantity of flowering increases with increasing levels of light.

(*C*) *Flower bud.*—Ellipsoidal; flowers perfect; spur is 4.5 cm long on average on mature bud, with the throat behind the ovary and originating from the major sepal. Bud length is 18 to 20 mm and bud diameter is 15 mm . Spur is Greyed-Purple Group 185C, spur tip is Greyed-Purple Group 185A, flower bud is Red Group 51A just before opening, and eye is Red-Purple Group 74D.

(*D*) *Flowers borne.*—On individual reddish purple pedicels 4.5 cm long from a whorl of usually five leaves. Flowering progressively around the whorls as buds and leaves develop. Leaf axils have one flower each.

(*E*) *Quantity of flowers.*—Numerous because of self-branching nature of plant and the long-lasting flower characteristic.

(*F*) *Diameter of flower.*—7.0 to 7.5 cm. Flower Depth: 5 mm.

(*G*) *Petals.*—(1) Shape: Heart. (2) Color: Top side when opening is Red Group 56B with a Red-Purple Group 74D eye, fading to Red Group 56D to White Group 155B; underside is White Group 155B with Red Group 54B midrib with standard petal having most color. (3) Number of petals: Five. (4) Size of petals: Standard: 4.5 cm wide and 3.0 cm long, two equal lobes with shallow cut. Wings: 4.0 cm wide and 3.0 cm long, two equal lobes with moderate cut. Keel: 4.5 cm wide and 3.5 cm long, two unequal lobes with deep cut.

(*H*) *Reproductive organs.*—(1) Stamens: Five in number. (a) Anther: Hooded shape, color is Yellow-White Group 158A with a Red-Purple Group 61C cast. (b) Pollen color: Yellow-White Group 158C. (2) Pistils: (a) Stigma: Five, segmented column, color is Red-Purple Group 62C. (b) Style color: White. (c) Ovaries: Five in number, size is 6 mm when immature, color is Greyed-Purple Group 185A.

(*I*) *Fertility.*—The plants are fertile, but do not normally set seed under greenhouse or garden conditions unless in a controlled crossing program.

Disease resistance: No significant disease or insect problems seen to date.

OTHER IMPORTANT CHARACTERISTICS

1. Self-branching, early flowering nature allows cultivar to be grown in 10 cm pots but is also vigorous enough to be grown in 15 to 25 cm containers as well.

2. Large overlapping petals result in a round flower that produces an attractive floral display.

3. Has shown the ability to tolerate both high temperatures and full sun and continue to bloom as demonstrated in Connellsville, Pa. summer trials and to bloom as well with cool night temperatures (5 to 10° C.) as demonstrated in outdoor trials in Lompoc, Calif., thus, extending the growing season.

I claim:

1. A new and distinct variety of Impatiens plant named Ovation Blush Pink, as illustrated and described.

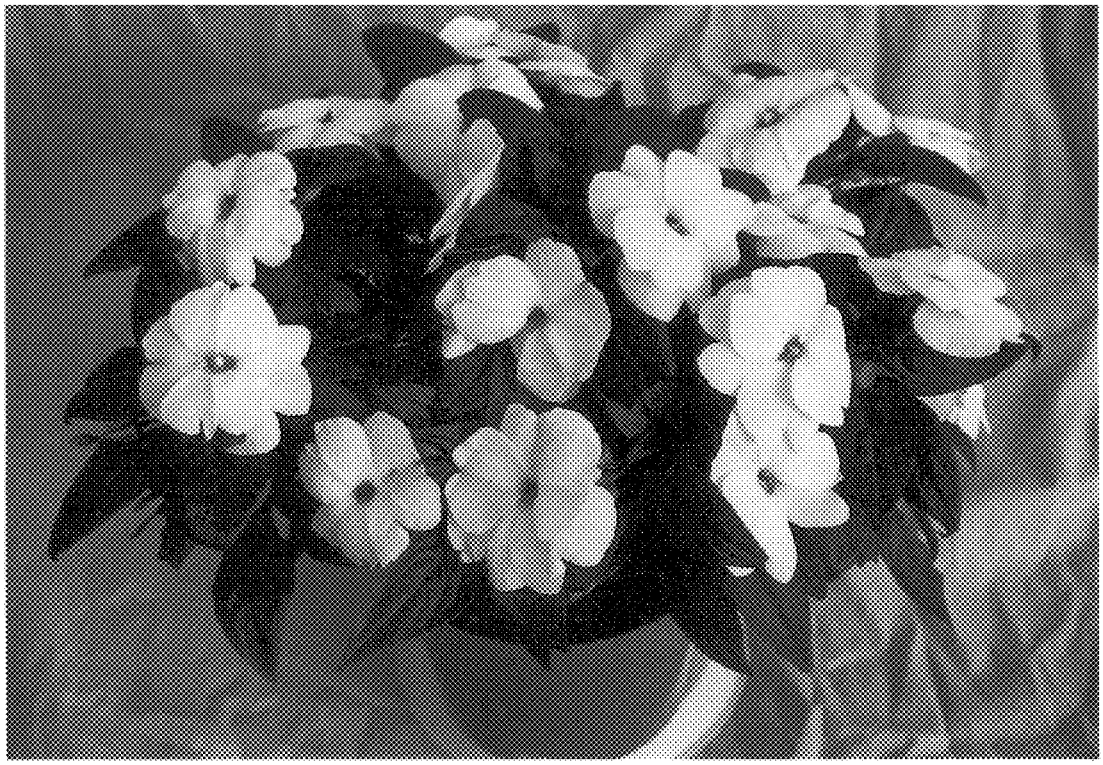

* * * * *